United States Patent
Wu et al.

(10) Patent No.: US 11,134,861 B2
(45) Date of Patent: Oct. 5, 2021

(54) EXERCISE STATE EVALUATION METHOD

(71) Applicants: Industrial Technology Research Institute, Hsinchu (TW); National Taiwan University of Sport, Taichung (TW)

(72) Inventors: Jian-Hong Wu, Nantou County (TW); Ren-Der Jean, Hsinchu (TW); Pin-Chou Li, Hsinchu (TW); Jyh-How Huang, Kaohsiung (TW); Jung-Hao Wang, New Taipei (TW); Szu-Ju Li, Changhua County (TW)

(73) Assignees: Industrial Technology Research Institute, Hsinchu (TW); National Taiwan University of Sport, Taichung (TW)

(*) Notice: Subject to any disclaimer, the term of this patent is extended or adjusted under 35 U.S.C. 154(b) by 161 days.

(21) Appl. No.: 16/541,163

(22) Filed: Aug. 15, 2019

(65) Prior Publication Data
US 2020/0054248 A1 Feb. 20, 2020

Related U.S. Application Data

(60) Provisional application No. 62/718,979, filed on Aug. 15, 2018.

(30) Foreign Application Priority Data

Jan. 17, 2019 (TW) .................. 108101755

(51) Int. Cl.
*A61B 5/103* (2006.01)
*A63B 24/00* (2006.01)
*A61B 5/11* (2006.01)

(52) U.S. Cl.
CPC ............ *A61B 5/1038* (2013.01); *A61B 5/112* (2013.01); *A63B 24/0006* (2013.01); *A61B 2562/0247* (2013.01); *A63B 2024/0012* (2013.01)

(58) Field of Classification Search
CPC ........ A63B 24/0006; A63B 2024/0012; A61B 5/0077; A61B 5/1038; A61B 5/112;
(Continued)

(56) References Cited

U.S. PATENT DOCUMENTS

| 5,111,410 A | 5/1992 | Nakayama et al. |
| 6,836,744 B1 | 12/2004 | Asphahani et al. |

(Continued)

FOREIGN PATENT DOCUMENTS

| CN | 107095677 | 8/2017 |
| EP | 2422698 | 2/2012 |

(Continued)

OTHER PUBLICATIONS

"Office Action of Taiwan Counterpart Application," dated Jan. 31, 2020, p. 1-p. 6.

*Primary Examiner* — Joshua Lee
(74) *Attorney, Agent, or Firm* — JCIPRNET

(57) ABSTRACT

An exercise state evaluation method having the following steps is provided. The steps includes: obtaining a plurality of sensing signals by a foot information sensing module; recording a receiving time of each of the sensing signals by a processing unit and generating a plurality of pressure values, a plurality of center of gravity values, and a center of gravity trajectory information corresponding a human body according to each of the sensing signals; determining a start time, an acting time and a finish time corresponding to an exercise according to the receiving time, the pressure values, the center of gravity values and the center of gravity
(Continued)

trajectory information; obtaining an act time value according to the start time, the acting time and the finish time; and integrating the pressure values, the center of gravity values, the center of gravity trajectory information and the act time value to an user interface.

10 Claims, 14 Drawing Sheets

(58) Field of Classification Search
CPC ... A61B 5/1122; A61B 5/1123; A61B 5/1128; A61B 5/6807; A61B 2503/10; A61B 2505/09; A61B 2562/0247
See application file for complete search history.

(56) References Cited

U.S. PATENT DOCUMENTS

| | | | |
|---|---|---|---|
| 8,571,827 | B2 | 10/2013 | Jang et al. |
| 8,941,723 | B2 | 1/2015 | Bentley et al. |
| 9,427,179 | B2 | 8/2016 | Mestrovic et al. |
| 9,526,946 | B1 * | 12/2016 | Zets ............... A61B 5/6892 |
| 9,591,993 | B2 | 3/2017 | Bamberg et al. |
| 9,694,238 | B2 | 7/2017 | Marty et al. |
| 9,817,439 | B2 | 11/2017 | Gosieski, Jr. et al. |
| 9,836,118 | B2 | 12/2017 | Steele |
| 9,962,593 | B1 * | 5/2018 | Massner ............... G01L 5/0052 |
| 2011/0054358 | A1 * | 3/2011 | Kim ............... A61B 5/1038 600/592 |
| 2014/0195023 | A1 * | 7/2014 | Statham ............... A61B 5/1038 700/91 |
| 2016/0029954 | A1 * | 2/2016 | Sato ............... A61B 5/6804 702/141 |
| 2016/0151696 | A1 * | 6/2016 | Chen ............... A63B 47/002 473/199 |
| 2016/0278683 | A1 * | 9/2016 | Naito ............... A61B 5/1121 |
| 2016/0287937 | A1 | 10/2016 | Fitzgerald et al. |
| 2016/0324445 | A1 * | 11/2016 | Kim ............... A61B 5/4528 |
| 2016/0345902 | A1 | 12/2016 | Degreef et al. |
| 2017/0061817 | A1 | 3/2017 | Mettler May |
| 2017/0232296 | A1 | 8/2017 | Niegowski et al. |
| 2017/0238845 | A1 * | 8/2017 | Wei ............... A61B 5/6829 |
| 2017/0239519 | A1 * | 8/2017 | Ishihara ............... A61B 5/22 |
| 2018/0028862 | A1 | 2/2018 | Statham et al. |
| 2019/0298226 | A1 * | 10/2019 | Filipowicz ............ A61B 5/0024 |

FOREIGN PATENT DOCUMENTS

| | | |
|---|---|---|
| TW | 201346238 | 11/2013 |
| TW | I455705 | 10/2014 |
| TW | 201515636 | 5/2015 |
| TW | M515864 | 1/2016 |
| TW | I566747 | 1/2017 |
| TW | M545407 | 7/2017 |
| TW | 201823721 | 7/2018 |

* cited by examiner

EXERCISE STATE EVALUATION METHOD

CROSS-REFERENCE TO RELATED APPLICATION

This application claims the priority benefit of U.S. provisional application Ser. No. 62/718,979, filed on Aug. 15, 2018, and Taiwan application serial no. 108101755, field on Jan. 17, 2019. The entirety of the above-mentioned patent applications is hereby incorporated by reference herein and made a part of this specification.

BACKGROUND

Technical Field

The disclosure relates to a digital analysis technique, and particularly relates to an exercise state evaluation method.

Description of Related Art

Exercise is accomplished through coordination of various parts of the body and a series of instantaneous movements. Taking baseball batting as an example, a batting movement must have a process from a preparation posture, observing and waiting for the ball, adjusting body parts to a batting position, lifting the foot, and swinging the bat to the final reset.

During the above process, an incorrect posture of batting may affect strength, an angle and a timing of batting, so that a batter cannot make a good use of his own advantages. More seriously, the wrong batting posture may result in injury to the batter and cause a permanent damage. However, since the instantaneous movements of batting are very short, and each person's body structure and force exertion habits are different, it is difficult for others to obtain accurate posture evaluation results through naked eye observation. Therefore, how to obtain accurate motion data through instruments and data for posture evaluation has gradually become an important issue in sports training.

SUMMARY

The disclosure is directed to an exercise state evaluation method including the following steps: obtaining a plurality of sensing signals corresponding to a human body by a foot information sensing module; recording a receiving time of each of the plurality of sensing signals by a processing unit and generating a plurality of pressure values, a plurality of center of gravity values, and center of gravity trajectory information corresponding to the human body according to each of the plurality of sensing signals; determining a start time, an acting time and a finish time corresponding to an exercise by the processing unit according to the receiving time and at least one of the plurality of pressure values, the plurality of center of gravity values and the center of gravity trajectory information; obtaining an act time value by the processing unit according to the start time, the acting time and the finish time; integrating the plurality of pressure values, the plurality of center of gravity values, the center of gravity trajectory information and the act time value by the processing unit, and providing an integration result to an user interface.

The disclosure is directed to an exercise state evaluation method including the following steps: obtaining a plurality of sensing signals corresponding to a human body by a foot information sensing module; recording a receiving time of each of the plurality of sensing signals by a processing unit and generating a plurality of pressure values, a plurality of center of gravity values, and center of gravity trajectory information corresponding to the human body according to each of the plurality of sensing signals; determining center of gravity counterweights at different receiving times corresponding to an exercise by the processing unit according to the receiving time and at least one of the plurality of pressure values, the plurality of center of gravity values and the center of gravity trajectory information; integrating the center of gravity counterweights by the processing unit for providing to an user interface; and sending a warning notification through the user interface by the processing unit when detecting that the center of gravity counterweight is changed from a first counterweight ratio to a second counterweight ratio.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
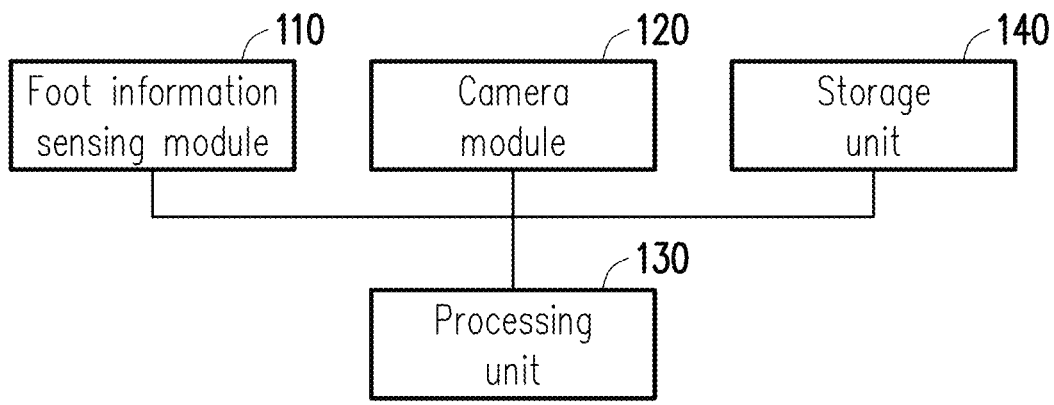
FIG. 1 is a schematic diagram of hardware implementing an exercise training assistant method according to an embodiment of the disclosure.

FIG. 1 is a schematic diagram of hardware implementing an exercise training assistant method according to an embodiment of the disclosure. Referring to FIG. 1, in an embodiment of the disclosure, the exercise training assistant method is commonly implemented through coordination of a foot information sensing module 110, a camera module 120, a processing unit 130 and a storage unit 140.

The foot information sensing module 110 is used for measuring motion data of foot movements of a corresponding testee. Particularly, in the embodiment of the disclosure, the foot information sensing module 110 has at least a foot bottom pressure sensor to detect a foot bottom pressure of the testee. For example, the foot information sensing module 110 may be implemented by pressure sensing chips mounted on, under or integrated in an insole. It should be noted that in order to make the measured data more accurate, the pressure sensing chips are at least disposed on a tiptoe, a heal, a left side and a right side of each insole. In the embodiment of the disclosure, the pressure sensing chips are further disposed in the left insole and the right insole in a uniform, non-overlapping manner and in close proximity.

In other embodiments of the disclosure, the foot information sensing module 110 also has various types of accelerometers, gyroscopes or a combination thereof. In the embodiment of the disclosure, the type or model number of the pressure sensing chips, the accelerometer and the gyroscope are not limited. Moreover, the disclosure is not limited to the type of the foot information sensing module 110.

The camera module 120 is used for recording images. Moreover, in the embodiment of the disclosure, the camera module 120 is installed in a sport field to record movement postures of the testee. The camera module 120 may be implemented with any type or any model number of the cameras, which is not limited by the disclosure.

The processing unit 130 is used for processing various types of information. In the embodiment of the disclosure, the processing unit 130 is, for example, a central processing unit (CPU), or other programmable general purpose or special purpose microprocessor, a digital signal processor (DSP), a programmable controller, etc., which is not limited by the disclosure.

The storage unit 140 is used for storing various information. Particularly, the storage unit 140 may store recorded exercise information of the testee. In the embodiment of the disclosure, the storage unit 140 is, for example (but is not limited to), any type of a fixed or movable random access memory (RAM), a read-only memory (ROM), a flash memory, a hard disk drive (HDD), a solid state drive (SSD) or a similar element or a combination of the above element.

Figure 2:
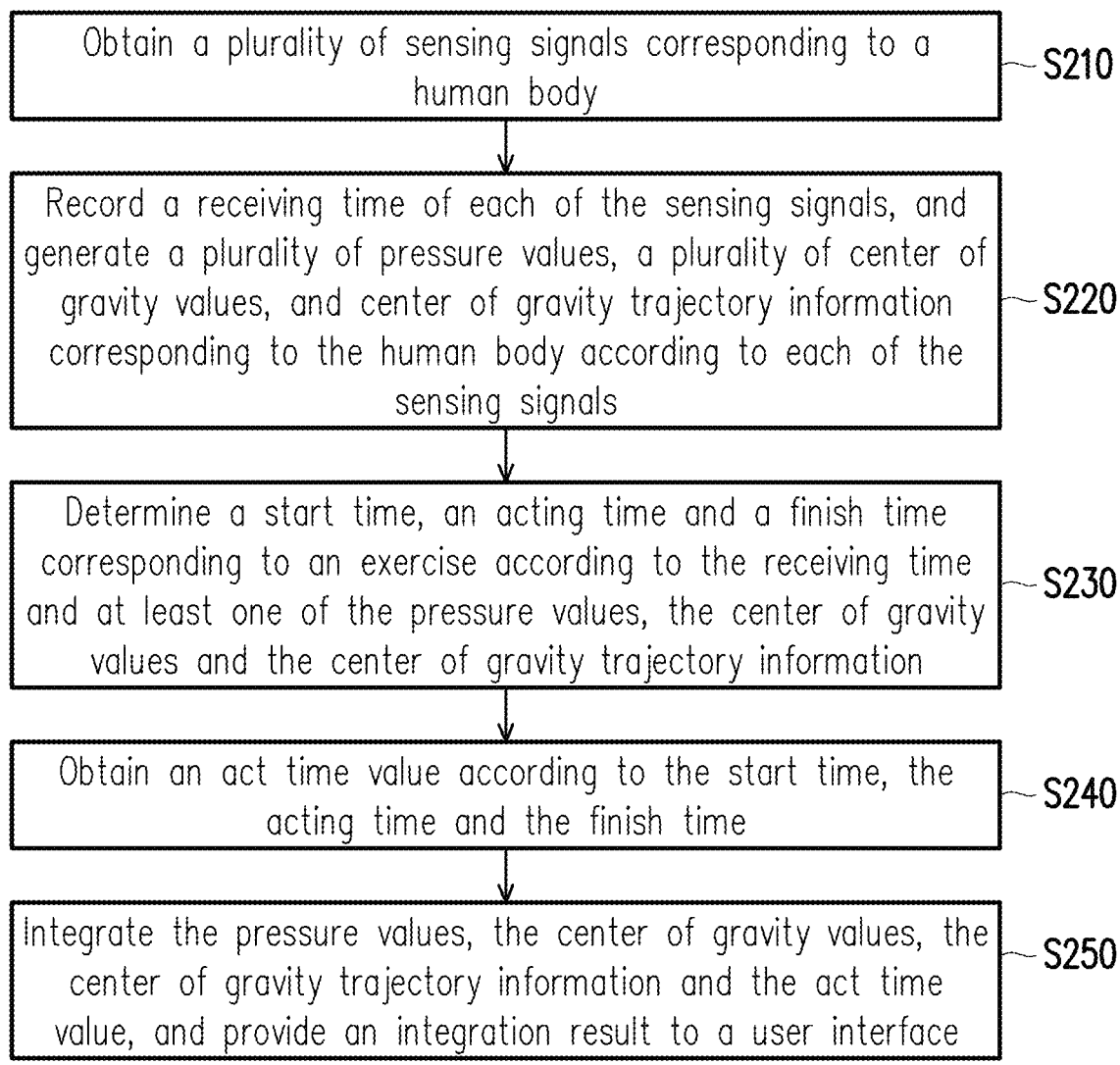
FIG. 2 is a flowchart illustrating an exercise state evaluation method according to an embodiment of the disclosure.

FIG. 2 is a flowchart illustrating an exercise state evaluation method according to an embodiment of the disclosure. Referring to FIG. 2, in a step S210, the foot information sensing module 110 obtains a plurality of sensing signals corresponding to a human body. In the embodiment, the foot information sensing modules 110 are respectively disposed in the insoles of the feet of the testee to obtain the sensing signals of pressures of the feet of the corresponding testee. It should be noted that in the embodiment of the disclosure, since the pressure sensing chips are disposed in the left insole and the right insole in the uniform, non-overlapping manner and in close proximity, the foot information sensing modules 110 may simultaneously acquire a plurality of sensing signals at a same time.

In a step S220, the processing unit 130 records a receiving time of each of the sensing signals, and generates a plurality of pressure values, a plurality of center of gravity values, and center of gravity trajectory information corresponding to the human body according to each of the sensing signals. To be specific, the foot information sensing module 110 transmits the received sensing signals to the processing unit 130. While the processing unit 130 receives the sensing signals, the processing unit 130 may record a system time corresponding to reception of each of the sensing signal. Alternatively, the processing unit 130 may build a time series by itself, for example, to build a first received sensing signal as a $0^{th}$ second, and sequentially sets the receiving time of each of the sensing signals according to a time difference between the subsequently received sensing signals and the first sensing signal. The receiving time values set by the processing unit 130 are not limited by the disclosure.

Moreover, since at the same time, the foot information sensing module 110 may simultaneously obtain a plurality of the sensing signals, the processing unit 130 may respectively obtain foot bottom pressure values of the testee according to the sensing signals. Moreover, since the processor sensing chips are distributed in many places of the insoles of the testee, the processing unit 130 may learn a foot bottom pressure distribution of the feet of the testee at each time through the pressure values. Further, the processing unit 130 may obtain a center of gravity value of the human body at each time according to the foot bottom pressure distribution of the feet of the testee, and accordingly obtain a center of gravity moving trajectory of the human body.

In a step S230, the processing unit 130 determines a start time, an acting time and a finish time corresponding to an exercise according to the receiving time and at least one of the pressure values, the center of gravity values and the center of gravity trajectory information. Although a posture and a force exertion method of each testee are different, in overall, however, variations in the pressure values, the center of gravity values and the center of gravity trajectory information are similar. Therefore, the processing unit 130 may determine the start time, the acting time and the finish time of the exercise according to at least one of the pressure values, the center of gravity values and the center of gravity trajectory information. A detailed process thereof is described later in the subsequent embodiment.

In a step S240, the processing unit 130 obtains an act time value according to the start time, the acting time and the finish time. After the start time, the acting time and the finish time are obtained, the processing unit 130 may not only obtain the act time value spent in the process from the start of the action to the end of the action, the processing unit 130 may further obtain a pre-action time value between the start time and the acting time.

In a step S250, the processing unit 130 integrates the pressure values, the center of gravity values, the center of gravity trajectory information and the act time value, and provides an integration result to a user interface. In this way, a coach may inspect a foot exercise state of the testee through the user interface, so as to provide corresponding gesture recommendations.

It should be noted that in an embodiment of the disclosure, in the exercise state evaluation method, the camera module 120 may further capture continuous image information corresponding to the human body. Therefore, the continuous image information and the sensing signals may correspond to a same action. Moreover, the continuous image information may be further transmitted to the processing unit 130 for processing.

The processing unit 130 analyzes the continuous image information to obtain an acting image in the continuous image information, and obtains a time corresponding to the acting image in the continuous image information according to the acting image.

The processing unit 130 integrates the continuous image information and the pressure values, the center of gravity values and the center of gravity trajectory information according to the acting time and the time corresponding to the acting image in the continuous image information. Namely, by pairing the acting motion in the image and the acting time determined according to the sensing signals, when the testee exercises, the images of the whole process and the pressure values of the feet, the center of gravity values and the center of gravity moving trajectory are integrated. In this way, when the coach selects a specific image frame or a specific pressure value, center of gravity value and center of gravity trajectory through the user interface, the corresponding pressure value, the center of gravity value and the center of gravity moving trajectory or the image frame may be simultaneously displayed. Alternatively, the coach may also specify a specific time through the user interface to accordingly display the corresponding image frame, the pressure value, the center of gravity value and the center of gravity moving trajectory.

Besides, in an embodiment of the disclosure, the processing unit 130 may further obtain an action standard model in the storage unit 140, and input the foot exercise state of the testee into the action standard model to compare the action standard model with the continuous image information and the pressure values, the center of gravity values and the center of gravity trajectory information, so as to generate a posture evaluation result. The posture evaluation result is that, for example, the center of gravity is too far forward, the hand is not raised high enough, the position of the hand is too close to the center of gravity, etc. Moreover, the processing unit 130 may further obtain an adjustment recommendation value for the reference of the testee. The disclosure is not limited to a representation method and content of the posture evaluation result.

A first embodiment and a second embodiment are provided below to describe how the processing unit 130 determines the start time, the acting time and the finish time corresponding to the exercise according to the receiving time and at least one of the pressure values, the center of gravity values and the center of gravity trajectory information.

Figure 3:
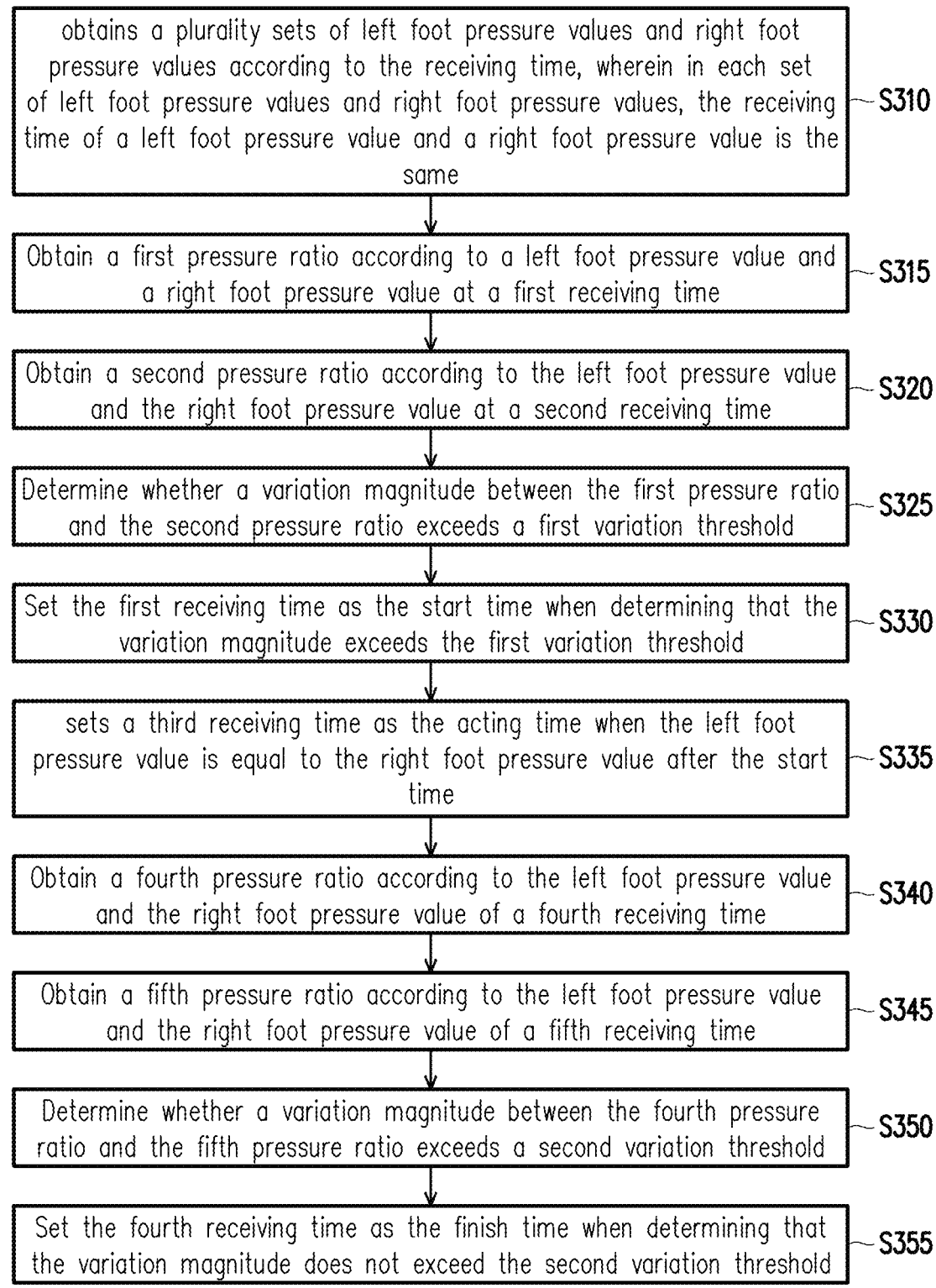
FIG. 3 is a flowchart illustrating an exercise state evaluation method according to a first embodiment of the disclosure.
Figure 4A:
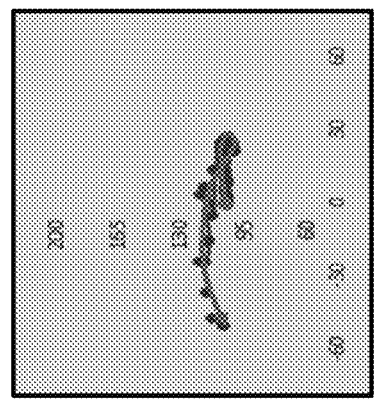
FIG. 4A to FIG. 4C are schematic diagrams of exercise states of the first embodiment of the disclosure.
Figure 4A:
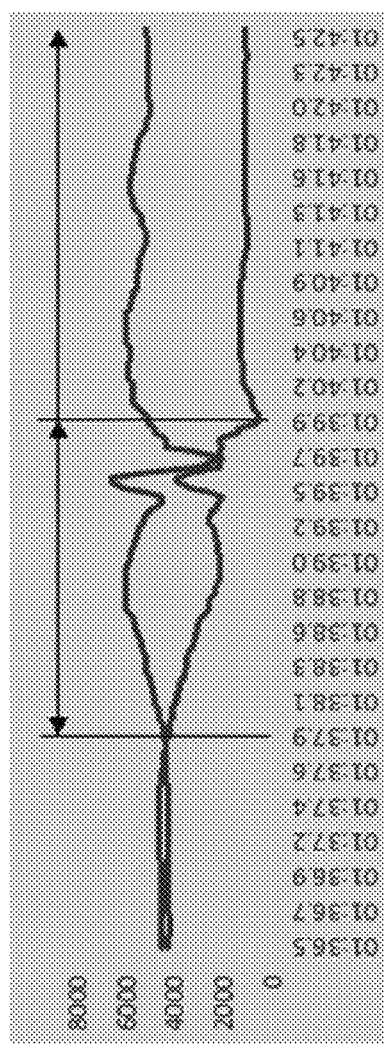
Figure 4B:
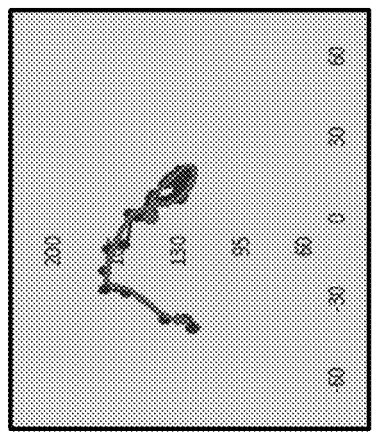
Figure 4B:
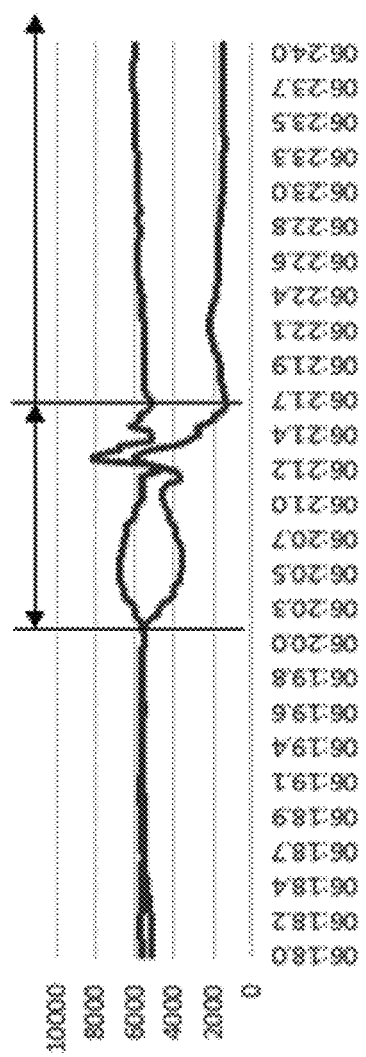
Figure 4C:
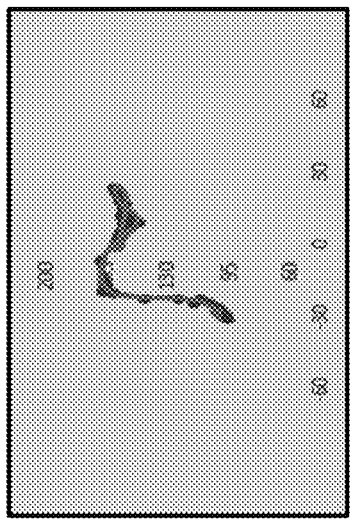
Figure 4C:
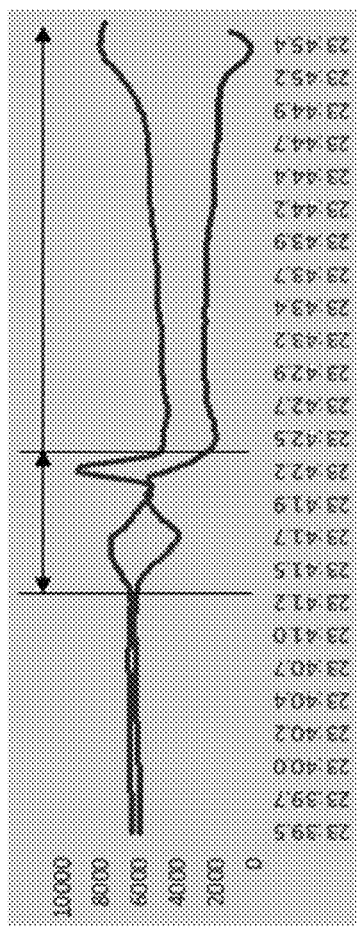

In the first embodiment, the type of the exercise is Golf. FIG. 3 is a flowchart illustrating an exercise state evaluation method according to the first embodiment of the disclosure. FIG. 4A to FIG. 4C are schematic diagrams of exercise states of the first embodiment of the disclosure. Referring to FIG. 3 to FIG. 4C.

In a step S310, the processing unit 130 obtains a plurality sets of left foot pressure values and right foot pressure values according to the receiving time, wherein in each set of left foot pressure values and right foot pressure values, the receiving time of a left foot pressure value and a right foot pressure value is the same. As described above, since the foot information sensing module 110 may simultaneously obtain a plurality of sensing signals generated by the pressure sensors distributed on the bottom of the foot, and each of the sensing signals have a corresponding pressure value, the processing unit 130 may respectively sum all of the pressure values on the bottom of the left foot and the pressure values of the right foot at each time point, and take the respectively summed pressure values as the left foot pressure value and the right foot pressure value. Moreover, the processing unit 130 may obtain the position of the center of gravity and the center of gravity value of the testee at each receiving time according to the pressure values simultaneously distributed on the bottoms of the feet, and sequentially connect the positions of the center of gravity of all of the time to obtain the center of gravity moving trajectory.

Referring to FIG. 4A, a left part of FIG. 4A presents the left foot pressure values and the right foot pressure values of the testee at different receiving time, and a right part of FIG. 4A presents the center of gravity moving trajectory of the testee.

In order to accurately define a foot bottom center of gravity coordinate range of the user, two-dimensional coordinates are used for defining the center of gravity coordinate range of the left and the right feet, for example, a left foot bottom center of gravity coordinate range is (−100-0, 0-255), a right foot bottom center of gravity coordinate range is (0-100, 0-255). To synthesize the ranges of the feet, the feet bottom center of gravity coordinate range is (−100-100, 0-255).

Based on the foot bottom center of gravity coordinate ranges, the processing unit 130 may calculate a left foot pressure center ($COP_l$) and a right foot pressure center ($COP_r$) under different actions to obtain a foot bottom pressure center (COP) according to the foot pressure distribution detected by the pressure sensors. To be specific, the processing unit 130 may list a left foot X coordinate as a negative value and a right foot X coordinate as a positive value according to the foot pressure distribution in collaboration with feet proportional counterweights, and respectively adds the X values and the Y values obtained after counterweight calculation to obtain a body weight center (center of gravity), and connects the coordinates in a time sequence to obtain the center of gravity moving trajectory.

In a step S315, the processing unit 130 obtains a first pressure ratio according to a left foot pressure value and a right foot pressure value at a first receiving time.

In a step S320, the processing unit 130 obtains a second pressure ratio according to the left foot pressure value and the right foot pressure value at a second receiving time.

To be specific, the first pressure ratio includes a left foot first pressure ratio and a right foot first pressure value. The processing unit 130 may first sum the left foot pressure value $P_l$ and the right foot pressure value $P_r$ at the first time to obtain a feet pressure value $P_t$ of the testee. Then, the processing unit 130 respectively obtains a left foot first pressure ratio $P_l/P_t$ and a right foot first pressure ratio $P_r/P_t$. A method that the processing unit 130 obtains the second pressure ratio is the same to the method of obtaining the first pressure ratio, and detail thereof is not repeated.

In a step S325, the processing unit 130 determines whether a variation magnitude between the first pressure ratio and the second pressure ratio exceeds a first variation threshold.

In a step S330, the processing unit 130 sets the first receiving time as the start time when determining that the variation magnitude exceeds the first variation threshold.

To be specific, in Golf playing, since a player (testee) may first spread the feet in situ while holding a club, and stay for a short period of time to prepare for swing. Moreover, when the player is ready, the player may swing and twist the waist, and now a center of gravity of the player is accordingly moved to cause a change of the pressure values of the feet. Therefore, when the processing unit 130 determines that the variation of the first pressure ratio and the second pressure ratio exceeds the first variation threshold, it represents that the center of gravity of the testee is moved, and the testee starts performing an action. Now, the processing unit 130 may set the first receiving time as the start time of such action. Taking FIG. 4A as an example, if the first variation threshold is ±5% (though the disclosure is not limited thereto), at a 01:37.9 second in the left part of FIG. 4A, the left foot pressure value and the right foot pressure value of the testee are almost the same, namely, the left foot first pressure ratio and the right foot first pressure ratio are all about 0.5. However, at a 01:38.1 second, the left foot pressure value of the testee exceeds 55% and the right foot pressure value of the testee is smaller than 45%. Therefore, the variation of the first pressure ratio and the second pressure ratio exceeds the first variation threshold of 5%, and the processing unit 130 takes the 01:37.9 second as the start time of the action.

It should be noted that in an embodiment, the processing unit 130 may further determine that the first pressure ratio is maintained within the first variation threshold for a period of time (for example, 2 seconds), and then executes the step S330. In this way, it is avoided to record other behaviors of the testee, such as non-exercise behaviors of walking, drinking, stretching, etc.

In a step S335, the processing unit 130 sets a third receiving time as the acting time when the left foot pressure value is equal to the right foot pressure value after the start time. In the embodiment, the acting time refers to a time when the club hits a ball. To be specific, taking a player with a posture of anterior left foot and posterior right foot as an example, the center of gravity is moved to the right foot when the player lifts the club. Moreover, when the player swings, by twisting the waist, the center of gravity of the body is moved from the right foot to the left foot, so that the body's force is brought forward. Therefore, the center of gravities of the left foot and the right foot are exchanged. Based on the above description, the processing unit 130 may determine that the third receiving time that the left foot pressure value is equal to the right pressure value (i.e. a time point of exchanging the center of gravities of the feet) and being after the start time is a time point of hitting the ball. Therefore, the processing unit 130 sets the third receiving time as the acting time.

In a step S340, the processing unit 130 obtains a fourth pressure ratio according to the left foot pressure value and the right foot pressure value of a fourth receiving time. In step S345, the processing unit 130 obtains a fifth pressure ratio according to the left foot pressure value and the right foot pressure value of a fifth receiving time. The methods that the processing unit 130 obtains the fourth pressure ratio and the fifth pressure ratio are the same to the method of obtaining the first pressure ratio of the step S315, and detail thereof is not repeated.

In a step S350, the processing unit 130 determines whether a variation magnitude between the fourth pressure ratio and the fifth pressure ratio exceeds a second variation threshold.

In a step S335, the processing unit 130 sets the fourth receiving time as the finish time when determining that the variation magnitude does not exceed the second variation threshold.

To be specific, after the player swings, the player releases the club to release the force of the body, and then retracts the club. During the club retraction, the body is maintained to a certain posture within a small period of time. Therefore, when the processing unit 130 detects that the variation between the fourth pressure ratio of the fourth receiving time and the fifth pressure ratio of the fifth receiving time does not exceed the second variation threshold after the acting time, it is regarded that the testee has retracted the club. Referring to FIG. 4A again, if the second variation threshold is ±5%, in the fourth pressure ratio obtained at the 01:39.9 second and the fifth pressure value obtained at the 01:40.02 second, the variations of the left foot and the right foot are all no more than 5%. Therefore, the processing unit 130 may set the 01:39.9 second as the finish time.

Moreover, in an embodiment, the processing unit 130 may further determine that the variation between the fourth pressure ratio of the fourth receiving time and the fifth pressure ratio of the fifth receiving time has to be maintained within a variation magnitude for a period of time (for example, 1 second) before determining that the testee is in a club retraction posture, so as to avoid reaching conclusions too quickly to make a mistake that the action is finished when the testee is still on the swing.

It should be noted that in the embodiment of the disclosure, the processing unit 130 may further use the center of gravity values and the center of gravity trajectory at the same time to assist determining the start time, the action time and the finish time. For example, only when the center of gravity of the testee is located in a specific region, or the center of gravity value is at a center of gravity position conformed with the start action, and are respectively complied with the conditions of the steps S315-S330, S335 and S340-S355, the start time, the action time and the finish time are accordingly determined. For example, the standard of the center of gravity value and the center of gravity position is that at the start time, a y-axis coordinate of the center of gravity position is around 100, and an x-axis coordinate of the center of gravity position is at a body center 0; at the action time, the y-axis coordinate of the center of gravity position is around 110, and the x-axis coordinate is at the left foot but biased to the body center −30-0; and at the finish time, the y-axis coordinate of the center of gravity position is around 120, and the center of gravity position is at the left foot. However, the disclosure is not limited thereto.

Referring to FIG. 4A to FIG. 4C again, it should be noted that in an actual application of the disclosure, FIG. 4A corresponds to an exercise record of a female player, FIG. 4B corresponds to an exercise record of a male player, and FIG. 4C corresponds to an exercise record of a coach. Based on FIG. 4A to FIG. 4C, it is obvious that the center of gravity moving trajectory of the female player is relatively flat, and the center of gravity moving trajectory of the coach is relatively undulating. Moreover, the pressures of the feet of the coach are relatively stable. Moreover, an interval between the start time and the action time of the female player is relatively long, and an interval between the start time and the action time of the coach is relatively short. Therefore, compared to the coach, the female player is lack of acceleration in swing, so that the ball cannot far enough. Therefore, the coach may integrate the information on the user interface through the processing unit 130, so as to adjust the posture of the player.

Figure 5:
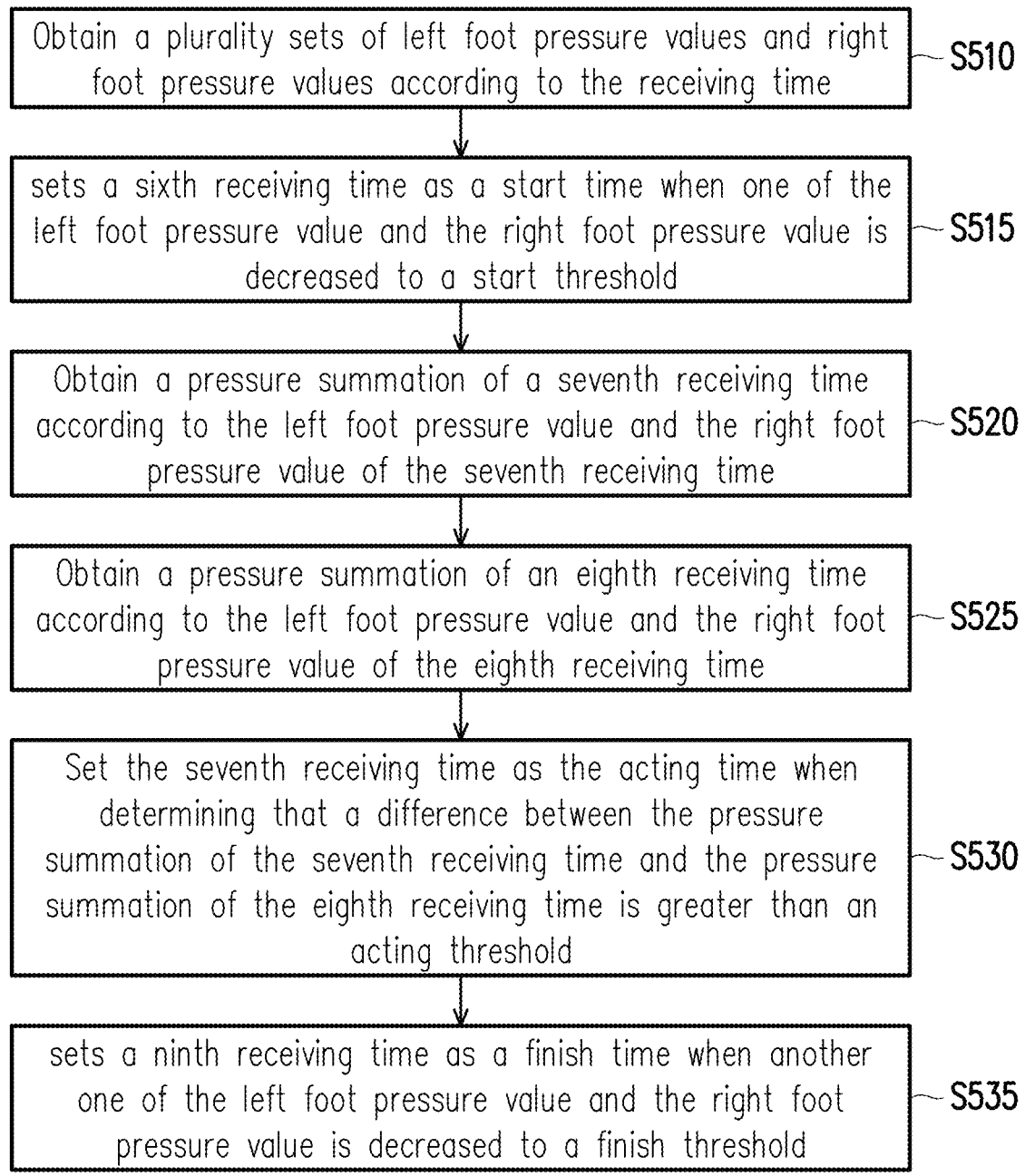
FIG. 5 is a flowchart illustrating an exercise state evaluation method according to a second embodiment of the disclosure.
Figure 6A:
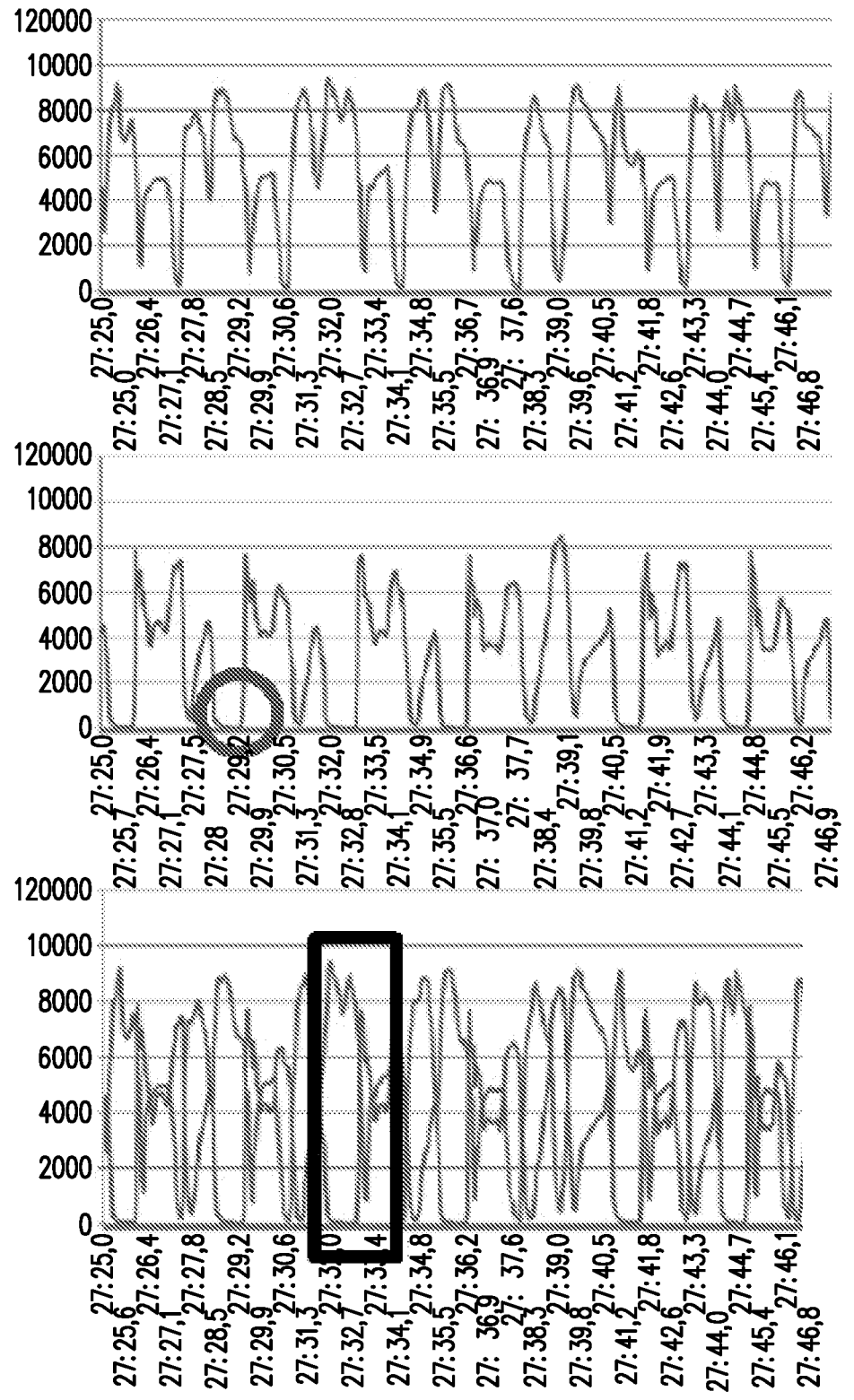
FIG. 6A to FIG. 6C are schematic diagrams of exercise states of the second embodiment of the disclosure.
Figure 6A:
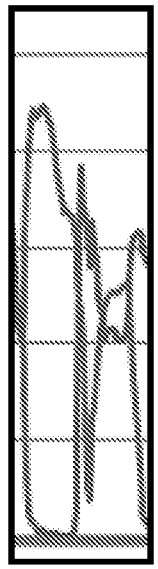
Figure 6B:
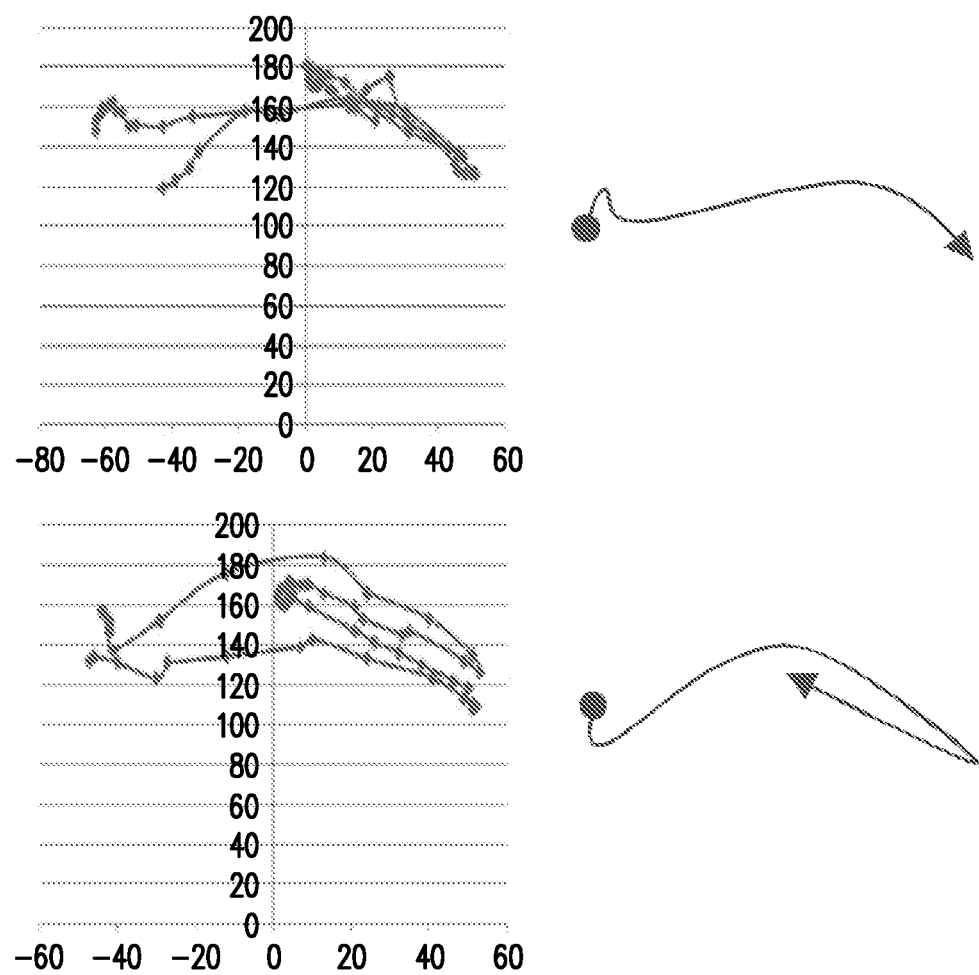
Figure 6C:
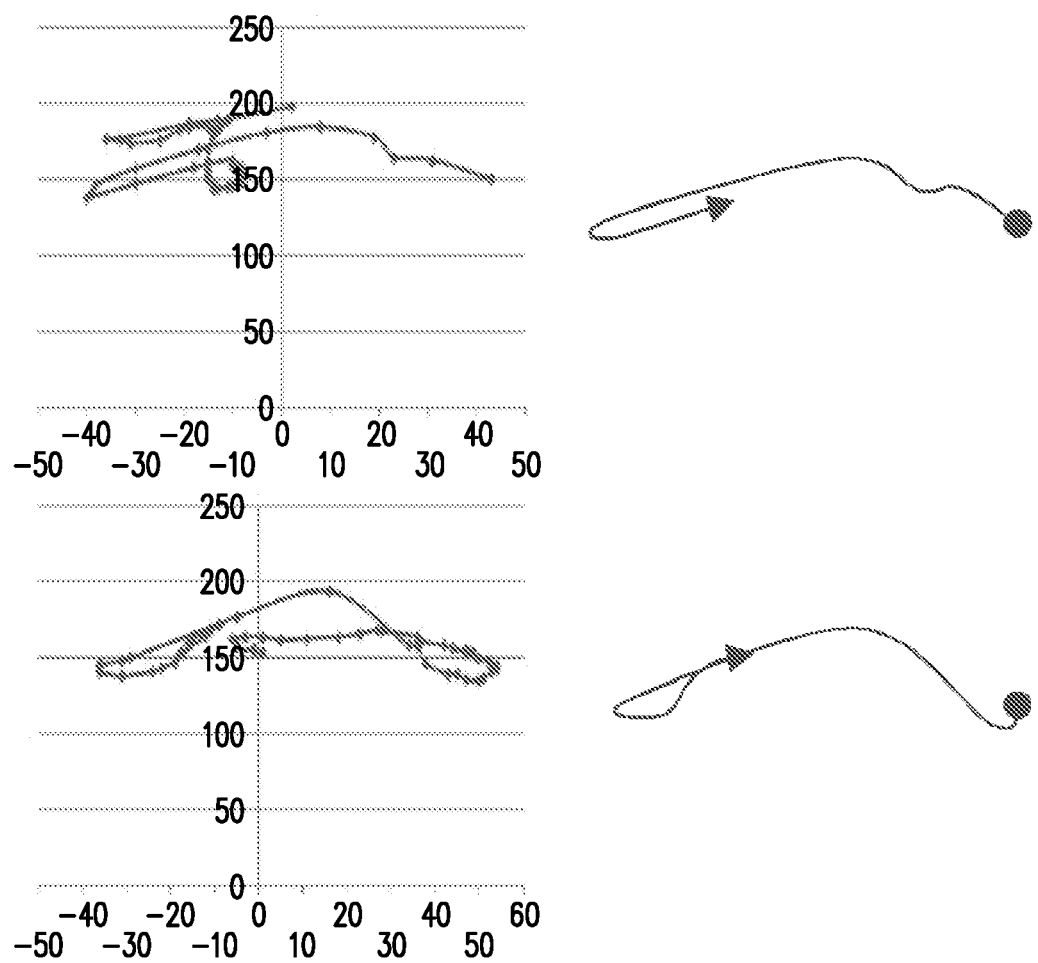

FIG. 5 is a flowchart illustrating an exercise state evaluation method according to a second embodiment of the disclosure. FIG. 6A to FIG. 6C are schematic diagrams of exercise states of the second embodiment of the disclosure. Referring to FIG. 5 to FIG. 6C, in the second embodiment, the exercise is, for example, a baseball batting.

In a step S510, the processing unit 130 obtains a plurality sets of left foot pressure values and right foot pressure values according to the receiving time. The step S510 is similar to the step S310, and detail thereof is not repeated. Moreover, referring to FIG. 6A, an upper left diagram illustrates the left foot pressure values of the testee at each time, a middle left diagram illustrates the right foot pressure values of the testee at each time, and a lower left diagram illustrates the feet pressure values of the testee at each time. Referring to FIG. 6B, the center of gravity moving trajectory of the testee may be integrated as that shown in FIG. 6B.

In a step S515, the processing unit 130 sets a sixth receiving time as a start time when one of the left foot pressure value and the right foot pressure value is decreased to a start threshold.

In detail, in the baseball exercise, a hitter will put the center of gravity on a back foot in a preparation posture, while the front foot touches the ground but remains in a flexible moving state. Therefore, when the processing unit 130 detects that the pressure value of one of the feet falls below the start threshold, the processing unit 130 determines that the hitter is in the preparation posture, and sets the corresponding sixth receiving time as the start time. Taking FIG. 6A as an example, in marked parts of the figure, it is clear that the pressure value of one foot is obviously decreased.

Moreover, in an embodiment of the disclosure, the processing unit 130 may further determine that the pressure ratio has to be maintained within a variation magnitude for a period of time (for example, 1 second) before determining that the testee is in the preparation posture, so as to avoid recording other behaviors of the testee, such as non-exercise behaviors of walking, drinking, stretching, etc.

Moreover, in the embodiment of the disclosure, the processing unit 130 may further use the center of gravity values and the center of gravity trajectory at the same time to assist determining the start time, i.e. only when the center of gravity of the testee is locate in a specific region, the start time is accordingly determined. For example, only when a y-axis coordinate of the center of gravity position is around 150-170, and an x-axis coordinate of the center of gravity position is between −10-10, and the condition of the step S510 is satisfied, the processing unit 130 sets the sixth receiving time as the start time. In this way, accuracy for recording the start time by the processing unit 130 is increased.

In a step S520, the processing unit 130 obtains a pressure summation of a seventh receiving time according to the left foot pressure value and the right foot pressure value of the seventh receiving time.

In a step S525, the processing unit 130 obtains a pressure summation of an eighth receiving time according to the left foot pressure value and the right foot pressure value of the eighth receiving time.

To be specific, the pressure summation of the seventh receiving time is a sum of the left foot pressure value and the right foot pressure value at the seventh receiving time, i.e. $P_r$. The pressure summation of the eighth receiving time is a sum of the left foot pressure value and the right foot pressure value at the eighth receiving time.

In step S530, when the processing unit 130 determines that a difference between the pressure summation of the seventh receiving time and the pressure summation of the eighth receiving time is greater than an acting threshold, the processing unit 130 sets the seventh receiving time as the acting time. To be specific, at the moment of batting, the front foot of the hitter is lifted. Now, an overall pressure of the whole body of the hitter is instantly decreased. Moreover, after the batting, the hitter's front foot may step forward, and the overall pressure of the whole body is instantly increased. Therefore, when the processing unit 130 determines that the difference between the pressure summation of the seventh receiving time and the pressure summation of the eighth receiving time is greater than the acting threshold, processing unit 130 determines that the hitter lifts the foot at the seventh receiving time, and accordingly sets the seventh receiving time as the acting time.

In a step S535, the processing unit 130 sets a ninth receiving time as a finish time that another one of the left foot pressure value and the right foot pressure value is decreased to a finish threshold. Since when the hitter completes the batting, the center of gravity of the hitter is moved from the back foot to the front foot, the pressure value of the back foot may be decreased. Therefore, the processing unit 130 may determine that the hitter completes the batting when the pressure value of the back foot is smaller than the finish threshold, and sets the corresponding ninth receiving time as the finish time.

Moreover, the processing unit 130 may further use the center of gravity values and the center of gravity trajectory at the same time to assist determining the finish time, i.e. only when the center of gravity of the testee is locate in a specific region, the start time is accordingly determined. For example, only when a y-axis coordinate of the center of gravity position is around 140, and an x-axis coordinate of the center of gravity position is between −10-10, and the condition of the step S510 is satisfied, the processing unit 130 sets the ninth receiving time as the finish time. In this way, accuracy for recording the finish time by the processing unit 130 is increased.

In an embodiment, the processing unit 130 may further determine that the pressure value of the back foot has to be maintained below the finish threshold for a period of time (for example, 1 second) before determining that the testee is in a batting complete posture, so as to avoid reaching conclusions too quickly to make a mistake that the action is finished when the testee is still on the batting.

It should be noted that FIG. 6B is a center of gravity trajectory actually measured when the player is a right-hand hitter, and FIG. 6C is a center of gravity trajectory actually measured when the player is a left-hand hitter. According to FIG. 6B and FIG. 6C, directions of the center of gravity trajectories of the left-hand hitter and the right-hand hitter are opposite.

Figure 7:
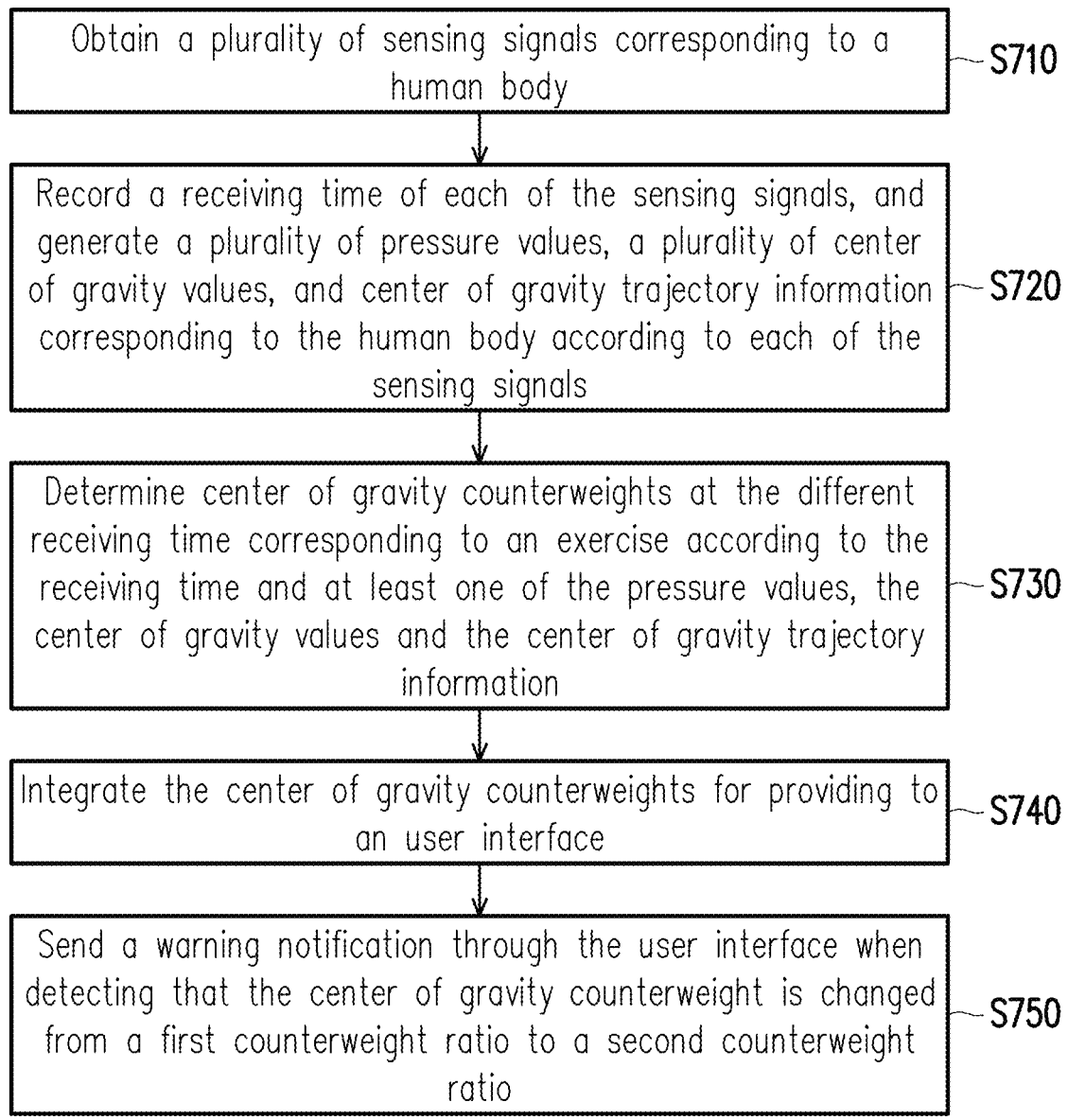
FIG. 7 is a flowchart illustrating an exercise state evaluation method according to another embodiment of the disclosure.

FIG. 7 is a flowchart illustrating an exercise state evaluation method according to another embodiment of the disclosure. Referring to FIG. 7, in a step S710, the foot information sensing module obtains a plurality of sensing signals corresponding to a human body.

In a step S720, the processing unit 130 records a receiving time of each of the sensing signals, and generates a plurality of pressure values, a plurality of center of gravity values, and center of gravity trajectory information corresponding to the human body according to each of the sensing signals. The step S710 to the step S720 are similar to the step S210 to the step S220, and details thereof are not repeated.

In a step S730, the processing unit 130 determines center of gravity counterweights at different receiving time corresponding to an exercise according to the receiving time and at least one of the pressure values, the center of gravity values and the center of gravity trajectory information. The step S730 is similar to the step S230, though it should be noted that after obtaining the feet pressure values of the testee, the processing unit 130 may further obtain the center of gravity counterweights of the testee according to the feet pressure values. For example, the center of gravity counterweights of the testee are respectively 45% and 55%. Details for the processing unit 130 obtaining the feet pressure values according to the sensing signals may refer to related description of the steps S315 and S320 corresponding to the step S230, and details thereof are not repeated.

In a step S740, the processing unit 130 integrates the center of gravity counterweights for providing to the user interface. In this way, the coach or a protector may view a state of the testee through the user interface displaying the center of gravity counterweight.

In a step S750, the processing unit 130 sends a warning notification through the user interface when the processing unit 130 detects that the center of gravity counterweight is changed from a first counterweight ratio to a second counterweight ratio.

To be specific, regardless of whether a person is walking, jogging or running, the center of gravity counterweight is almost the same under a body balance state. Therefore, if the center of gravity counterweight of the testee is obviously different, it may be that the foot of the testee is injured, causing the testee to shift the center of gravity falling on the injured part to the uninjured part. Therefore, if the processing unit 130 detects that the center of gravity counterweight is changed from the first counterweight ratio to the second counterweight ratio, it is reasonable to suspect that the testee is injured. Therefore, the processing unit 130 sends the warning notification through the user interface. The warning notification is, for example, a sound notification, an image message notification, etc., which is not limited by the disclosure. Moreover, in order to find out the injury situation of the player more accurately, in an embodiment of the disclosure, the processing unit 130 may further determine whether a variation magnitude between the first counterweight ratio and the second counterweight ratio is greater than a warning threshold (for example, 30%). Namely, if the first counterweight ratio is 0.45:0.55, the second counterweight ratio is 0.65:0.35, the variation magnitude between the first counterweight ratio and the second counterweight ratio is now greater than the warning threshold, so that the processing unit 130 sends the warning notification through the user interface.

Moreover, in the embodiment, the processing unit 130 may further determine whether the second counterweight ratio is maintained for a period of time (for example, 1 minute). In this way, it is avoided to sends a wrong warning notification by the processing unit 130 through the user interface when the testee simply wants to stretch and change the posture, or temporarily changes the center of gravity due to a special condition on the road.

Figure 8A:
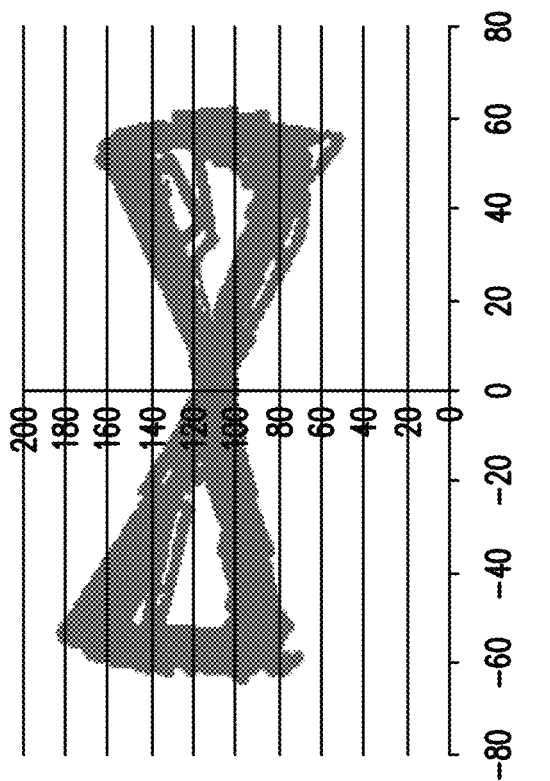
FIG. 8A to FIG. 8D are schematic diagrams of exercise states of an exercise state evaluation method according to an embodiment of the disclosure.
Figure 8A:
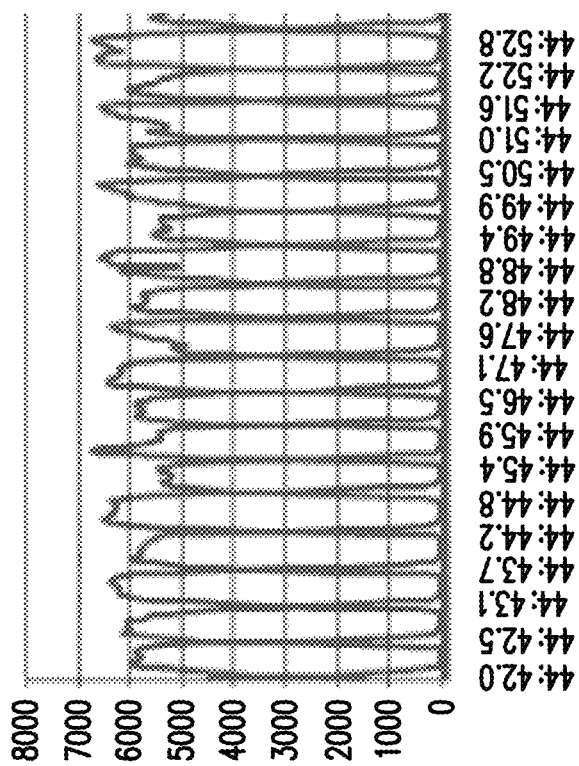
Figure 8B:
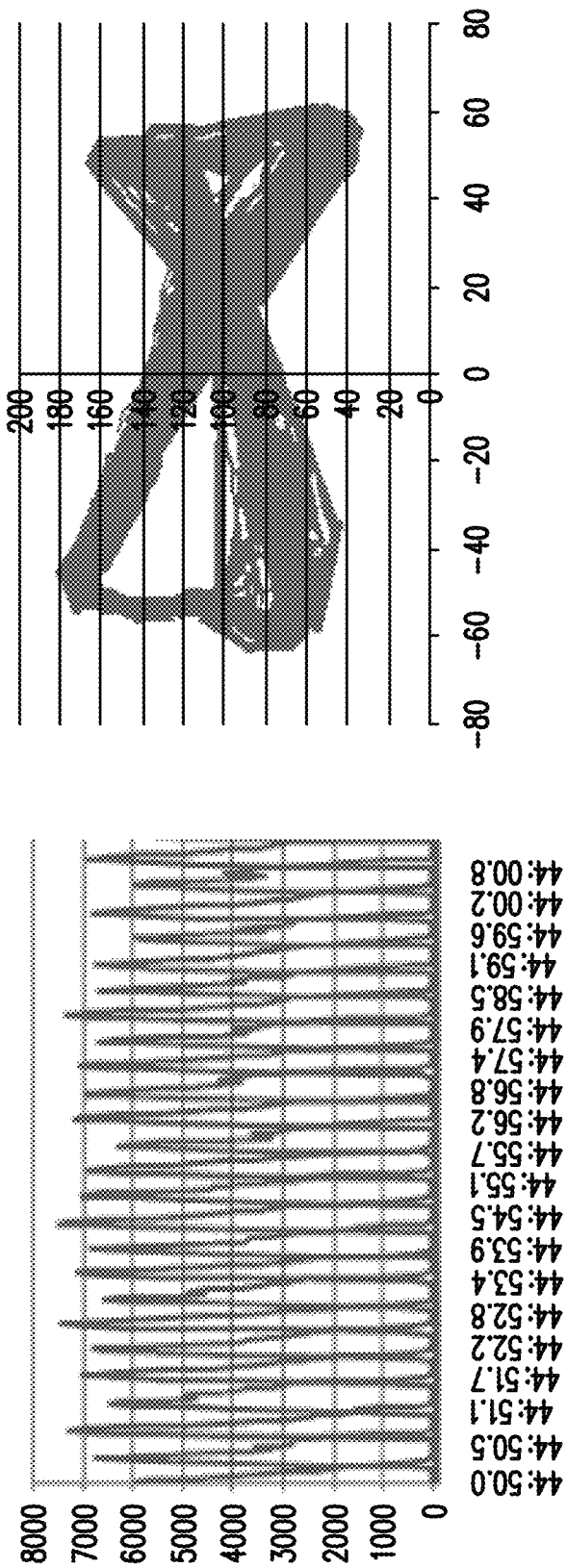
Figure 8C:
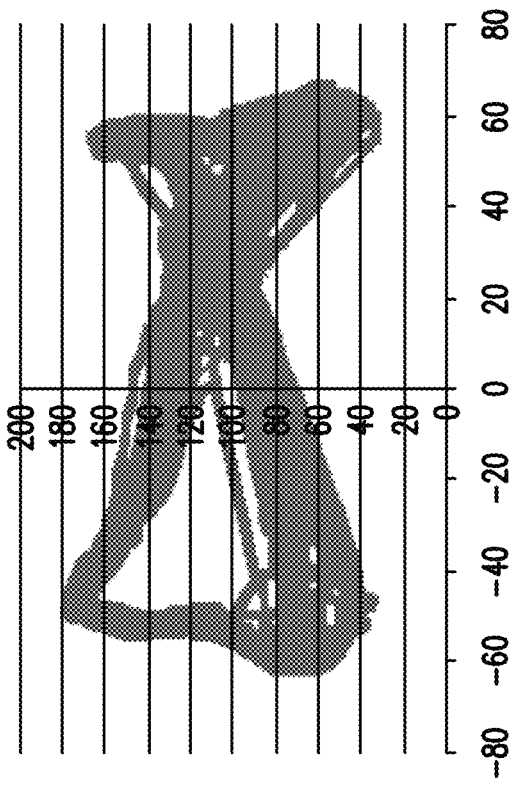
Figure 8C:
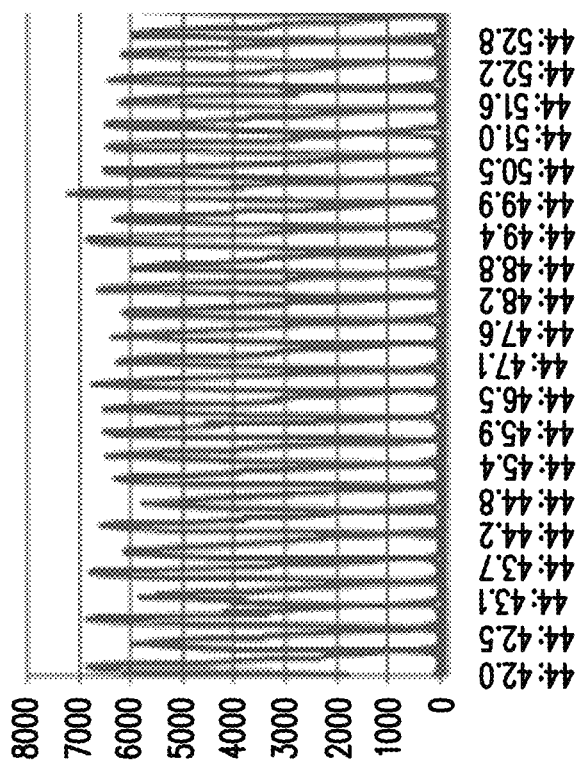
Figure 8D:
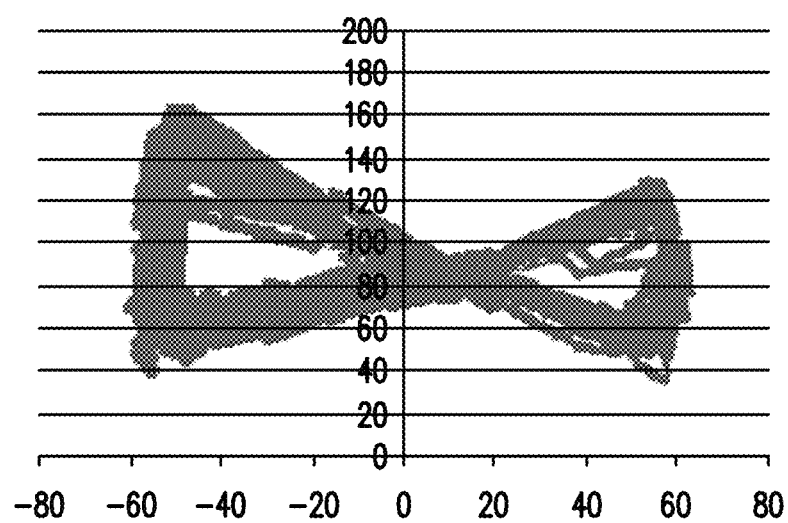

Referring to FIG. 8A to FIG. 8D, FIG. 8A to FIG. 8D are schematic diagrams of exercise states of the exercise state evaluation method according to an embodiment of the disclosure. FIG. 8A to FIG. 8C illustrate feet pressure values (left diagrams) and center of gravity moving trajectories (right diagrams) obtained when the testee is in a walking, jogging and running state. FIG. 8D is a schematic diagram of a possible center of gravity moving trajectory obtained when the testee is injured and in the walking state.

In FIG. 8A to FIG. 8C, it is obvious that when the testee is walking, a stride rate of the testee is relatively low, and the stride rate is higher in running. Moreover, in case of walking or running, the testee may present similar center of gravity trajectories, i.e. butterfly shape moving trajectories. However, in case of jogging and running, an area of the butterfly shape is larger, and the center of gravity of the user is more obvious. Namely, in case of jogging and running, shift of the center of gravity of the testee is relatively drastic.

In FIG. 8D, when the testee is injured, compared to the center of gravity moving trajectory of FIG. 8A, sizes of the left and right butterflies are obvious different, and the center of gravity is obviously changed.

It should be noted that in some embodiments of the disclosure, the foot information sensing module 110 further includes an accelerometer and a gyroscope. The foot information sensing module 110 receives an acceleration sensing value and an angular velocity sensing value, and the processing unit 130 integrates the acceleration sensing value and the angular velocity sensing value for providing to the user interface. In detail, through the accelerometer, the processing unit 130 may further obtain a foot vector of the testee according to data measured by the accelerometer. For example, the left foot of the testee may unconsciously move towards the front left, so that the testee may be biased to the left when walking straight. Through the gyroscope, the processing unit 130 may further get to learn an angle between the heel and the ground when the heel is lifted, or an angle between the toe and the ground when the toe is lifted during the walking or running process of the testee.

Besides, the exercise state evaluation method of the disclosure is adapted to all kinds of fixed-point ball batting exercises, which may automatically record the start time, the acting time, and the finish time of the corresponding exercise based on the attributes of the fixed-point ball batting exercise. Alternatively, the exercise state evaluation method of the disclosure is also adapted to various exercises such as marathon, running, football, etc., so as to immediately react to foot injury of the athlete.

It will be apparent to those skilled in the art that various modifications and variations can be made to the disclosed embodiments without departing from the scope or spirit of the disclosure. In view of the foregoing, it is intended that the disclosure covers modifications and variations provided they fall within the scope of the following claims and their equivalents.

What is claimed is:

1. An exercise state evaluation method, comprising:
   obtaining a plurality of sensing signals corresponding to a human body by a foot information sensing module;
   recording a receiving time of each of the plurality of sensing signals by a processing unit, and generating a plurality of pressure values, a plurality of center of gravity values, and center of gravity trajectory information corresponding to the human body according to each of the plurality of sensing signals;
   determining a start time, an acting time and a finish time corresponding to an exercise by the processing unit according to the receiving time and at least one of the plurality of pressure values, the plurality of center of gravity values and the center of gravity trajectory information;
   obtaining an act time value by the processing unit according to the start time, the acting time and the finish time; and
   integrating the plurality of pressure values, the plurality of center of gravity values, the center of gravity trajectory information and the act time value by the processing unit, and providing an integration result to a user interface.

2. The exercise state evaluation method as claimed in claim 1, further comprising:
   capturing continuous image information corresponding to the human body by a camera module;
   analyzing the continuous image information by the processing unit to obtain an acting image in the continuous image information, and obtaining a time corresponding to the acting image in the continuous image information according to the acting image; and
   integrating the continuous image information and the plurality of pressure values, the plurality of center of gravity values and the center of gravity trajectory information by the processing unit according to the acting time and the time corresponding to the acting image in the continuous image information.

3. The exercise state evaluation method as claimed in claim 2, further comprising:
   obtaining an action standard model in a storage unit by the processing unit, and comparing the action standard model with the continuous image information and the plurality of pressure values, the plurality of center of gravity values and the center of gravity trajectory information to generate a posture evaluation result.

4. The exercise state evaluation method as claimed in claim 1, wherein the step of determining the start time, the acting time and the finish time corresponding to the exercise by the processing unit according to the receiving time and at least one of the plurality of pressure values, the plurality of center of gravity values and the center of gravity trajectory information further comprises:

obtaining a plurality sets of left foot pressure values and right foot pressure values by the processing unit according to the receiving time, wherein in each set of the plurality sets of left foot pressure values and right foot pressure values, the receiving time of a left foot pressure value and a right foot pressure value is the same;

obtaining a first pressure ratio by the processing unit according to the left foot pressure value and the right foot pressure value of a first receiving time;

obtaining a second pressure ratio by the processing unit according to the left foot pressure value and the right foot pressure value of a second receiving time;

determining whether a variation magnitude between the first pressure ratio and the second pressure ratio exceeds a first variation threshold by the processing unit; and setting the first receiving time as the start time by the processing unit in response to determining that the variation magnitude exceeds the first variation threshold.

5. The exercise state evaluation method as claimed in claim 4, wherein the step of determining the start time, the acting time and the finish time corresponding to the exercise by the processing unit according to the receiving time and at least one of the plurality of pressure values, the plurality of center of gravity values and the center of gravity trajectory information further comprises:

setting a third receiving time as the acting time when the left foot pressure value is equal to the right foot pressure value and being after the start time by the processing unit.

6. The exercise state evaluation method as claimed in claim 4, wherein the step of determining the start time, the acting time and the finish time corresponding to the exercise by the processing unit according to the receiving time and at least one of the plurality of pressure values, the plurality of center of gravity values and the center of gravity trajectory information further comprises:

obtaining a fourth pressure ratio by the processing unit according to the left foot pressure value and the right foot pressure value of a fourth receiving time;

obtaining a fifth pressure ratio by the processing unit according to the left foot pressure value and the right foot pressure value of a fifth receiving time;

determining whether a variation magnitude between the fourth pressure ratio and the fifth pressure ratio exceeds a second variation threshold by the processing unit; and setting the fourth receiving time as the finish time by the processing unit in response to that the variation magnitude does not exceed the second variation threshold.

7. The exercise state evaluation method as claimed in claim 1, wherein the step of determining the start time, the acting time and the finish time corresponding to the exercise by the processing unit according to the receiving time and at least one of the plurality of pressure values, the plurality of center of gravity values and the center of gravity trajectory information further comprises:

obtaining a plurality sets of left foot pressure values and right foot pressure values by the processing unit according to the receiving time, wherein in each set of the plurality sets of left foot pressure values and right foot pressure values, the receiving time of a left foot pressure value and a right foot pressure value is the same; and setting a sixth receiving time as the start time when one of the left foot pressure value and the right foot pressure value is decreased to a start threshold by the processing unit.

8. The exercise state evaluation method as claimed in claim 7, wherein the step of determining the start time, the acting time and the finish time corresponding to the exercise by the processing unit according to the receiving time and at least one of the plurality of pressure values, the plurality of center of gravity values and the center of gravity trajectory information further comprises:

obtaining a pressure summation of a seventh receiving time by the processing unit according to the left foot pressure value and the right foot pressure value of the seventh receiving time;

obtaining a pressure summation of an eighth receiving time by the processing unit according to the left foot pressure value and the right foot pressure value of the eighth receiving time; and setting the seventh receiving time as the acting time by the processing unit in response to that a difference between the pressure summation of the seventh receiving time and the pressure summation of the eighth receiving time is greater than an acting threshold.

9. The exercise state evaluation method as claimed in claim 7, wherein the step of determining the start time, the acting time and the finish time corresponding to the exercise by the processing unit according to the receiving time and at least one of the plurality of pressure values, the plurality of center of gravity values and the center of gravity trajectory information further comprises:

setting a ninth receiving time as the finish time when another one of the left foot pressure value and the right foot pressure value is decreased to a finish threshold.

10. The exercise state evaluation method as claimed in claim 1, further comprising:

receiving an acceleration sensing value and an angular velocity sensing value by the foot information sensing module; and integrating the acceleration sensing value and the angular velocity sensing value by the processing unit for providing to the user interface.

* * * * *